US010052381B2

(12) United States Patent
Bernal-Mizrachi

(10) Patent No.: US 10,052,381 B2
(45) Date of Patent: Aug. 21, 2018

(54) CLASSIFIERS OF NF-κB PATHWAY ACTIVATION, DEVICES, AND METHODS OF USE THEREOF

(71) Applicant: Emory University, Atlanta, GA (US)

(72) Inventor: Leon Bernal-Mizrachi, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/482,353

(22) Filed: Apr. 7, 2017

(65) Prior Publication Data

US 2017/0209572 A1    Jul. 27, 2017

Related U.S. Application Data

(63) Continuation of application No. 14/414,507, filed as application No. PCT/US2013/060872 on Sep. 20, 2013, now abandoned.

(60) Provisional application No. 61/703,354, filed on Sep. 20, 2012.

(51) Int. Cl.
| | | |
|---|---|---|
| *C12Q 1/68* | (2018.01) | |
| *A61K 39/395* | (2006.01) | |
| *A61K 31/675* | (2006.01) | |
| *A61K 31/704* | (2006.01) | |
| *A61K 31/475* | (2006.01) | |
| *A61K 31/573* | (2006.01) | |
| *C07K 16/28* | (2006.01) | |
| *A61K 39/00* | (2006.01) | |

(52) U.S. Cl.
CPC ...... *A61K 39/39541* (2013.01); *A61K 31/475* (2013.01); *A61K 31/573* (2013.01); *A61K 31/675* (2013.01); *A61K 31/704* (2013.01); *C07K 16/2887* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| 7,166,639 B2 | 1/2007 | Wan |
| 2007/0105136 A1 | 5/2007 | Staudt |
| 2009/0203050 A1 | 8/2009 | Bonavida |
| 2011/0223157 A1 | 9/2011 | Schafer |

FOREIGN PATENT DOCUMENTS

WO    2012031008    3/2012

OTHER PUBLICATIONS

Tomita et al (Leukemia & Lymphoma, 2006, 47(6): 1041-1047).*
Guo et al (Journal of Clinical Oncology, 2011, 29(10): e257-e261).*
Johnson et al (Blood, 2008, 112: 477; 6 internet pages).*
Marcheselli et al (Leukemia & Lymphoma, 2011, 52(10): 1867-1872).*
Alizadeh et al. Distinct types of diffuse large B-cell lymphoma identified by gene expression profiling, Nature. 2000, 403(6769):503-11.
Auphan et al. Immunosuppression by glucocorticoids: inhibition of NF-kappa B activity through induction of I kappa B synthesis. Science. 1995, 270(5234):286-90.
Bernal et al. The role of NF-κb-1 and NF-κB-2-mediated resistance to apoptosis in lymphomas, PNAS, 2006, 103 (24) 9220-9225.
Brune et al. Origin and pathogenesis of nodular lymphocyte-predominant Hodgkin lymphoma as revealed by global gene expression analysis, Journal of Experimental Medicine,2008, 205 (10) 2251-2268.
Campagno et al. Mutations of multiple genes cause deregulation of NF-kappaB in diffuse large B-cell lymphoma, Nature, 2009, 459, 717-721.
Davis et al. Constitutive nuclear factor kappaB activity is required for survival of activated B cell-like diffuse large B cell lymphoma cells, J Exp Med. 2001, 194(12):1861-74.
De et al. Tissue-microarray based immunohistochemical analysis of survival pathways in nodular sclerosing classical Hodgkin lymphoma as compared with Non-Hodgkin's lymphoma, Int J Clin Exp Med, 2010, 3(1):55-68.
Gene Expression Omnibus (GEO), GSE24020, NF-κB suppresses genomic instability in non-Hodgkin lymphomas, 2010.
Guo et al. Canonical Nuclear Factor kapaB Pathway Links Tumorigenesis of Synchronous Mantle-Cell Lymphoma, Clear-Cell Renal-Cell Carcinoma, and GI Stromal Tumor, Journal of Clinical Oncology, vol. 29, No. 10, 2011: pp. e257-e261.
Guo et al. Molecular impact of selective NFKB1 and NFKB2 signaling on DLBCL phenotype, Oncogene (2017) 36, 4224-4232.
Ho et al. (2005) MALT1 and the API2-MALT1 fusion act between CD40 and IKK and confer NF-kappa B-dependent proliferative advantage and resistance against FAS-induced cell death in B cells. Blood 7: 2891-99.
Jais et al. The expression of 16 genes related to the cell of origin and immune response predicts survival in elderly patients with diffuse large B-cell lymphoma treated with CHOP and rituximab, Leukemia (2008) 22, 1917-1924.
Johnson et al. Deletion in Chromosome 17p12 and Gains in Chrmosome 9q33.3 by Array Comparative Hybridization are Associated with R-CHOP Treatment Failure, Blood 2008 112:477.
Keller et al. (2000) Inhibition of NF-kappaB induces apoptosis of KSHV-infected primary effusion lymphoma cells. Blood 7: 2537-42.
Mathas et al. Elevated NF-κB p50 complex formation and Bcl-3 expression in classical Hodgkin, anaplastic large-cell, and other peripheral T-cell lymphomas, Blood, 2005, 106:4287-4293.

(Continued)

*Primary Examiner* — Sean E Aeder
(74) *Attorney, Agent, or Firm* — Emory Patent Group

(57) ABSTRACT

This disclosure relates to classifiers of NF-κB pathway activation, devices, and methods of use thereof. In certain embodiments, the disclosure relates to methods comprising measuring changes in expression of genes controlled by p105 in a sample providing a detected p105 controlled gene expression pattern. In certain embodiments, the methods further comprise measuring changes in expression of genes controlled by p100 in a sample providing a detected p100 controlled gene expression pattern. In certain embodiments, the methods further comprise the step of comparing the detected p105 controlled gene expression patterns to a predetermined gene pattern and/or the detected p100 controlled gene expression patterns to a predetermined pattern.

2 Claims, 9 Drawing Sheets

(56) References Cited

OTHER PUBLICATIONS

Nishikori, Classical and Alternative NF-κB Activation Pathways and Their Roles in Lymphoid Malignancies, J.Clin. Exp. Hematopathol, 2005, vol. 45, No. 1, 15-24.

Rosenwald et al. Gene expression profiling of diffuse large B-cell lymphoma. Leuk Lymphoma. 2003;44 Suppl 3: S41-7.

Rosenwald et al. Molecular diagnosis of primary mediastinal B cell lymphoma identifies a clinically favorable subgroup of diffuse large B cell lymphoma related to Hodgkin lymphoma. J Exp Med. 2003, 198(6):851-62.

Savinova et al. The Nfkb1 and Nfkb2 Proteins p105 and p100 Function as the Core of High-Molecular-Weight Heterogeneous Complexes, Molecular Cell 34, 591-602, 2009.

Tomita et al. Phase II study of CHOP-GR therapy for advancedstage follicular lymphoma, Leukemia & Lymphoma, 47:6, 1041-1047, 2006.

Viatour et al. NF-kappaB2/p100 induces Bcl-2 expression, Leukemia, 2003, 17, 1349-1356.

Wang et al. Common Gene Variants in the Tumor Necrosis Factor (TNF) and TNF Receptor Superfamilies and NF-κB Transcription Factors and Non-Hodgkin Lymphoma Risk, PLoS ONE 4(4): e5360.

Yu et al. The Biological Functions of NF-κB1 (p50) and its Potential as an Anti-Cancer Target, Curr Cancer Drug Targets, 2009, 9(4): 566-571.

\* cited by examiner

| Cluster 1 | | Cluster 2 | | |
|---|---|---|---|---|
| p105 | p100 | p100 | p105 | |
| HLA-F | NFE2L | EIF4E | USP1 | CCNA2 |
| HLA-E | NCOA1 | HSPD1 | DNAJC9 | MAD2L1 |
| ICAM-1 | JUNB | SFRS3 | BRIX1 | KIF11 |
| ZFAND3 | RASSF4 | COX11 | CCDC99 | ECT2 |
| LMNA | C2 | SEH1L | FAM29A | |
| FAM65A | PLXND1 | SETMAR | MCM10 | |
| BIRC7 | DENND3 | NIP7 | C12orf48 | |
| EXD3 | PPARD | | PBK | |
| SYNPO | | | MSH2 | |
| TNS4 | | | DHFR | |

| Dataset | Variable (p105 as reference) | Hazard Ratio 95% CI | P value |
|---|---|---|---|
| Lenz et al GSE10846) | P100 classifier * | 1.784 (1.182, 2.694) | 0.0059 |
| | P100 classifier ** | 1.402 (0.907, 2.166) | 0.1281 |
| | P100 classifier *** | 1.310 (0.776, 2.211) | 0.3116 |

CLASSIFIERS OF NF-κB PATHWAY ACTIVATION, DEVICES, AND METHODS OF USE THEREOF

CROSS-REFERENCE TO RELATED APPLICATIONS

This application is a continuation of U.S. application Ser. No. 14/414,507 filed Jan. 13, 2015, which is the National Stage of International Application No. PCT/US2013/060872 filed Sep. 20, 2013, which claims the benefit of priority to U.S. Provisional Application No. 61/703,354 filed Sep. 20, 2012. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 11134USCON_ST25.txt. The text file is 2 KB, was created on Apr. 7, 2017, and is being submitted electronically via EFS-Web.

BACKGROUND

The mammalian nuclear factor kappa beta (NF-κB) system consists of five NF-κB subunits—RelA, c-Rel, RelB, p50, and p52—and five proteins with inhibitory activity—IκBa, IκBb, IκB3, p105, and p100. NF-κB subunits interact with each other forming homo- and heterodimers. The NF-κB1 and NF-κB2 proteins, p105 and p100, are the precursors of p50 and p52. The rate of processing of the p105 and p100 regulates the availability of NF-κB dimers (Savinova et al., 2009, Mol Cell 34, 591-602). The degradation of inhibitory proteins bound to the NF-κB subunits leads to translocation of the NF-κB homo- or heterodimers into the nucleus. Here, they initiate transcription of NF-κB-controlled genes, resulting in pro-inflammatory responses and signals for cell survival and proliferation (Nishikori 2005, J Clin Exp Hematol 45: 15-24). Activation of the NF-κB pathway with a nuclear translocation of NF-κB dimers containing p50 is typically referred to as the classical (or canonical, or p105) NF-κB activation pathway. Similarly, activation of the NF-κB pathway with a nuclear translocation of NF-κB dimers containing p52 is typically referred to as the alternative (or noncanonical, or p100) NF-κB activation pathway (Nishikori 2005, J Clin Exp Hematol 45: 15-24).

NF-κB pathway activation can be induced under physiological conditions by stimulation of cells with certain ligands, or due to intrinsic dysregulation of the molecular machinery controlling the NF-κB system. For example, mutations discovered in positive and negative regulators of NF-κB can constitutively activate the NF-κB pathway (Compagno et al., 2009, Nature 459, 717-721). Activation of NF-κB is detected in a number of human lymphomas, including adult T-cell lymphoma and B cell lymphomas, such as primary mediastinal B cell lymphomas, primary effusion lymphoma, mucosa-associated lymphoid tissue lymphoma, primary effusion lymphoma, a subtype of non-Hodgkins lymphoma, diffuse large B cell lymphoma (DLBCL), and activated B cell like (ABC) DLBCL (Davis et al., 2001, J Exp Med 12: 1861-74; Alizadeh et al., 2000, Nature 6769: 503-11; Rosenwald et al., 2003, Leuk Lymphoma pp S41-S47; Rosenwald et al., 2003, J Exp Med 6: 851-62; Ho et al., 2005; Blood 7: 2891-99; Keller et al., 2000, Blood 7: 2537-42; Wang et al, 2009, PLoS ONE 4(4):e5360. Epub 2009 Apr. 24). NF-κB activation leads to suppression of anti-apoptotic pathways and production of pro-inflammatory cytokines that further induce proliferation of lymphoid cells (Wang et al, 2009, PLoS ONE 4(4):e5360. Epub 2009 Apr. 24; Auphan et al, 1995, Science 5234, 286-90).

Treatments for these diverse types of lymphomas vary from surgery, chemotherapy, hormonal therapy, radiation treatment, and more recently, immunotherapy with agents such as rituximab (US2011/0223157; Stockdale 1998, Medicine, Vol 3, Rubenstein and Federman eds., Chapter 12, Section IV; US2009/0203050). See also. U.S. Pat. No. 7,166,639 and US2011/0223157. However, each of these therapies, or therapy combinations, has its own drawbacks for the patients, including toxicity and systemic immunosuppression. Different patients respond differently to the same therapy and overall survival of patients varies. Thus, there is a need to identify improved diagnostic and therapeutic methods.

A number of gene expression and tissue characterization methods have been developed to classify different lymphoma types based on their molecular signature. Such classifications may help predict the patients' responses to particular therapies. See US2011/0223157, US2007/0105136, US2009/0203050, and De and Brown, 2010, Int J Clin Exp Med 3: 55-68.

SUMMARY

This disclosure relates to classifiers of NF-κB pathway activation, devices, and methods of use thereof. In certain embodiments, the disclosure relates to methods comprising measuring changes in expression of genes controlled by p105 canonical NF-κB pathway in a sample providing a detected p105 controlled gene expression pattern. In certain embodiments, the methods further comprise measuring changes in expression of genes controlled by p100 noncanonical NF-κB pathway in a sample providing a detected p100 controlled gene expression pattern. In certain embodiments, the methods further comprise the step of comparing the detected p105 controlled gene expression patterns to a predetermined gene pattern and/or the detected p100 controlled gene expression patterns to a predetermined pattern.

In certain embodiments, the disclosure relates to the samples obtained from a subject diagnosed with a disease, wherein the disease is cancer, and wherein the cancer is a lymphoma. In certain embodiments, the lymphoma is selected from a B cell neoplasm, T cell and natural killer cell neoplasm, multiple myeloma, and Hodgkin lymphoma.

In certain embodiments, the method comprising measuring changes in expression of genes controlled by p105 comprises detecting the expression of three or more genes selected from, four or more genes selected from, or five or more genes selected from EXD3, BIRC7, HLA-F, PBK, DHFR, ECT2, and CCDC99. In certain embodiments, the method comprising measuring changes in expression of genes controlled by p100 comprises detecting the expression of three or more genes selected from, four or more genes selected from, or five or more genes selected from NIP7, COX11, HSPD1, EIF4E, NFE2L1, JUNB, and RASSF4. In certain embodiments, the method comprising measuring changes in expression of genes controlled by p105 further comprises detecting the expression of three or more genes selected from, four or more genes selected from, five or more genes selected from, six or more genes selected from, seven or more genes selected from, eight or more genes selected from, nine or more genes selected from, ten or more genes selected from, eleven or more genes selected from, twelve or more genes selected from, thirteen or more genes selected from, fourteen or more genes selected from, or fifteen or more genes selected from HLA-F, HLA-E, ICAM-1, ZFAND3, LMNA, FAM65A, EXD3, SYNPO, TNS4, NFE2L1, NCOA1, JUNB, RASSF4, C2, PLXND1, DENND3, PPARD. In certain embodiments, the method comprising measuring changes in expression of genes controlled by p100 comprises detecting the expression of three or more genes selected from, four or more genes selected from, five or more genes selected from, six or more genes selected from, seven or more genes selected from, eight or more genes selected from, nine or more genes selected from, ten or more genes selected from, eleven or more genes selected from, twelve or more genes selected from, thirteen or more genes selected from, fourteen or more genes selected from, fifteen or more genes selected from, sixteen or more genes selected from, or seventeen or more genes selected from EIF4E, SFRS3, SEH1L, SETMAR, USP1, DNAJC9, BRIX1, CCDC99, FAM29A, MCM10, C12orf48, PBK, MSH2, DHFR, CCNA2, MAD2L1, KIF11, and ECT2.

In certain embodiments, the method comprising measuring changes in expression of genes controlled by p105 and p100 comprises detecting Rel A and Rel B nuclear intensity (AI). In certain embodiments, a receiver operating characteristic curve may be used to determine the capacity of Rel A/Rel B AI ratio in predicting the activation of the pathway detected by the gene classifier. In other embodiments, the percent of agreement between the two methods of detection of activation of the NF-κB pathways may be determined using different cutoff points for different sensitivities and specificities based on the Rel A/Rel B ratio.

In certain embodiments, the method further comprises the step of recording a normal, decreased, or increased expression of the gene(s). In certain embodiments, the method comprises the step of reporting the results, e.g., recorded expression, to a medical professional, medical institution, or a subject from which the sample was obtained or representative thereof.

In certain other embodiments, the method further comprises the step of administering antibody against CD20 in the event that the detected p105 controlled gene expression pattern indicates a canonical NF-κB activation pattern, and wherein the antibody against CD20 is rituximab. In certain embodiments, the antibody against CD20 is administered in combination with another anticancer agent.

In certain embodiments, measuring changes in expression of genes controlled by p105 or p100 comprises obtaining a tissue sample from a human subject. In certain embodiments, measuring changes in expression of genes controlled by p105 or p100 further comprises extracting total ribonucleic acid (RNA) from said tissue sample, utilizing said RNA in gene expression analysis assay, such as microarray, and obtaining expression levels for expressed genes. In certain embodiments, the method comprises comparing said expression levels obtained from said tissue sample to expression levels generated by a sample with a predetermined gene expression pattern. In certain embodiments, said predetermined gene expression pattern is a pattern produced by cell lines, wherein said cell lines are OCI-LY3 or Daudi.

In certain other embodiments, the disclosure relates to a device comprising hybridization probes for detecting measuring changes in expression of genes controlled by p105 or by p100. In certain embodiments, said hybridization probes consist essentially of oligonucleotide sequences for HLA-F, HLA-E, ICAM-1, ZFAND3, LMNA, FAM65A, EXD3, SYNPO, TNS4, NFE2L1, NCOA1, JUNB, RASSF4, C2, PLXND1, DENND3, and PPARD genes. In certain embodiments, said hybridization probes consist essentially of oligonucleotide sequences for EIF4E, SFRS3, SEH1L, SETMAR, USP1, DNAJC9, BRIX1, CCDC99, FAM29A, MCM10, C12orf48, PBK, MSH2, DHFR, CCNA2, MAD2L1, KIF11, and ECT2 genes.

In certain other embodiments, the disclosure relates to a kit comprising hybridization probes for detecting measuring changes in expression of genes controlled by p105 or by p100. In certain embodiments, the kit further comprises solutions for RNA isolation, reverse-transcription, amplification, labeling, hybridization and washing to remove unhybridized material.

In certain other embodiments, the disclosure relates to a method comprising predicting an overall survival of a patient receiving rituximab, cyclophosphamide, doxorubicin hydrochloride (hydroxydaunorubicin), vincristine sulfate (Oncovin), and prednisone (RCHOP) therapy and having a sample with changes in expression of genes controlled by p105 or p100. In certain embodiments, a patient with said treatment with changes in expression of genes controlled by p105 will have a better overall predicted survival than a patient with said treatment with changes in expression of genes controlled by p100.

DETAILED DISCUSSION

Figure 1A:
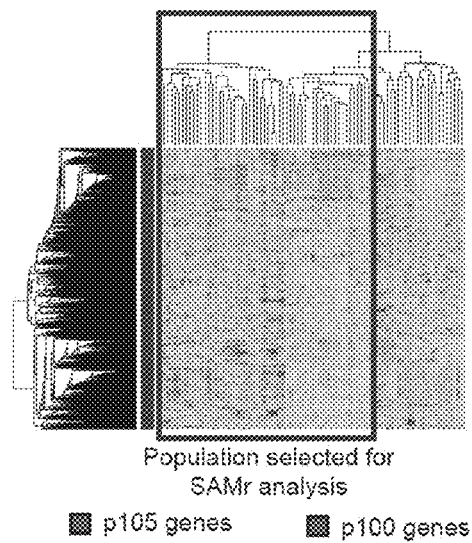
FIG. 1A illustrates the development of p100 and p105 classifiers. The image Image intensity displaying the expression levels of genes most highly weighted included in the p100 and p105 target gene list in a DLBCL published dataset (GSE4475). Data were logy transformed and quantile normalized prior to analysis.

This disclosure relates to classifiers of NF-κB pathway activation, devices, and methods of use thereof. In certain embodiments, the disclosure relates to methods comprising measuring changes in expression of genes controlled by p105 in a sample providing a detected p105 controlled gene expression pattern. In certain embodiments, the methods further comprise measuring changes in expression of genes controlled by p100 in a sample providing a detected p100 controlled gene expression pattern.

The following detailed description is intended to illustrate the various embodiments for making and using the classifiers described in the disclosure. As such, this detailed description is not meant to be limiting of the scope or application of the embodiments listed herein. It will be understood by persons skilled in the art that numerous modifications, substitutions, changes, or replacements with equivalents may be made to the particulars of the disclosure without altering the scope of the embodiments, and that such equivalents are to be included herein.

Terms

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

The term "nucleic acid" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term is used to designate a single molecule, or a collection of molecules. Nucleic acids may be single stranded or double stranded, and may include coding regions and regions of various control elements. The term "oligonucleotide" generally refers to a short length of single-stranded nucleic acid usually less than 30 nucleotides long, although it may also be used interchangeably with the term "polynucleotide."

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

The term "amplification" is the action of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide or nucleic acid of interest. A probe may be single-stranded or double-stranded. Probes are useful in the detection, identification and isolation of particular gene sequences. The term "probe" may also refer to a protein having a capacity to bind to particular sequences of nucleotides or amino acids. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present disclosure be limited to any particular detection system or label.

The terms "protein" and "polypeptide" refer to compounds comprising amino acids joined via peptide bonds and are used interchangeably.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "measuring" refers to an action of performing necessary steps to detect relative quantity of an entity in a given sample at a given time when that entity has a property of being present in variable quantities at various times. As such, the term "measuring changes in expression of genes" refers to an action of performing necessary steps (such as nucleic acid isolation, labeling, hybridization to specific probes for a given set of genes, and detection of the labeled and hybridized nucleic acids to specific probes) to detect changes, both increases and decreases, in expression levels of genes of interest.

The term "microarray" refers to an array that is limited to a small area. Typically, such arrays are limited to no more than about 1 inch by 3 inches, as they are frequently generated on microscope slides. Microarrays contain the maximum number of spots which can be created within the limits; typically, this number is less for hand-generated arrays than it is for robotically or machine-generated arrays. A typical machine-generated array contains up to about 10,800 spots.

The term "microarray" and the method for "microarray hybridization" are detailed by L. M. Staudt in U.S. Pat. No. 7,711,492 B2 as follows. Microarray refers to a plurality of nucleic acid probes coupled to the surface of a substrate in different but known locations. The substrate is made preferably of a solid compound. Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the gene expression product from the sample. This gene expression product may be, for example, total cellular mRNA, rRNA, or cDNA obtained by reverse transcription of total cellular mRNA. The gene expression product from a sample is labeled with a radioactive, fluorescent, or other label to allow for detection. Following hybridization, the microarray is washed, and hybridization of gene expression product to each nucleic acid probe on the microarray is detected and quantified using a detection device such as a phosphorimager or scanning confocal microscope.

There are two broad classes of microarrays: cDNA and oligonucleotide arrays. cDNA arrays consist of hundreds or thousands of cDNA probes immobilized on a solid support.

These cDNA probes are usually 100 nucleotides or greater in size. These cDNA microarrays are simultaneously hybridized with two fluorescent cDNA probes, each labeled with a different fluorescent dye (typically Cy3 or Cy5). In this format, the relative mRNA expression in two samples is directly compared for each gene on the microarray. Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques. The solid support for oligonucleotide arrays is typically a glass or silicon surface.

Microarrays may generally be produced using a variety of techniques, such as mechanical or light directed synthesis methods that incorporate a combination of photolithographic methods and solid phase synthesis methods. Microarrays may be packaged in such a manner as to allow for diagnostic use, or they can be an all-inclusive device. Microarrays directed to a variety of purposes are commercially available from Affymetrix (Affymetrix, Santa Clara, Calif.). For instance, these microarrays may be used for genotyping and gene expression monitoring for a variety of eukaryotic and prokaryotic species.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) Molecular Cloning: A Laboratory Manual, Cold Spring Harbor Press, NY, pp 9.31 9.58).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39 7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

As used herein, "subject" refers to any animal, preferably a human patient, livestock, or domestic pet.

As used herein, the terms "treatment", "treat" and "treating" are not limited to the case where the subject (e.g. patient) is cured and the disease is eradicated. Rather, embodiments of the present disclosure also contemplate treatment that merely reduces symptoms, and/or delays disease progression.

Gene Signature as Predictor of Activation of the Canonical and Noncanonical Pathways The present disclosure indicates that DLBCL can be segregated according to the activation of the canonical and noncanonical NF-κB pathways. Furthermore, the disclosure identifies that enrichment of canonical (p105) NF-κB target genes can predict a better outcome of RCHOP treatment. The most likely explanation is the exclusive suppression of canonical NF-κB target genes produced by rituximab and the association of noncanonical (p100) NF-κB target-enriched patients with ABC phenotype, higher proliferation rates and probability for Burkitt's gene expression pattern. This disclosure further substantiates the basis of a more precise algorithm that could match therapy with specific disease mechanisms in DLBCL.

The verification methods used to evaluate the capacity of the p100 and p105 classifiers to predict the status of the noncanonical and canonical pathway demonstrated a strong agreement with the molecular basis of the tumors and mouse models. In tumors, the fraction of cases (7%) presenting with a discordant immunofluorescence and gene expression results can be related to signals originating from non-tumor cells in the microenviroment. However, this is arguable because among cells from normal and tumor lymph nodes, normal lymphocytes demonstrated the lowest nuclear levels of Rel A and B. Indeed, others have shown that normal germinal center B cells do not express NF-κB target genes highly, suggesting that the "noise" signal produced by normal infiltrating cells may be minimal, compared to the overall signal obtained by both methods of detection. Hence, this difference may reflect a higher sensitivity of the genomic approach presented in the disclosure or limitations in the method of IF signal detection, image processing and staining. Taken together, these results strongly support the conclusion that these NF-κB classifiers reliably reflect the status of activation of these signals under different circumstances. Hence, the p100 and p105 classifiers can serve as useful tools for screening specific pathway inhibitors in DLBCL.

The p100 and p105 classifiers identified in the present disclosure with genomic analysis and immunofluorescence method provide a better understanding of the breadth of engagement that these pathways have in ABC and GCB DLBCL tumors. The differential engagement of the NF-κB pathways in ABC and GCB DLBCL identified in the disclosure further supports and extends recent reports that show nuclear localization of the NF-κB subunits, p50 and p52, in ABC, GCB and unclassified DLBCL. These findings, combined with the parallel clustering of the disclosed p105 classifier and a published NF-κB signature, substantiate a shift in paradigm from the belief that ABC DLBCL has an exclusive activation of the NF-κB pathway into a more broad observation that includes GCB DLBCL and the noncanonical NF-κB pathway. This observation is of relevance, based on the fact that underlying the activation of the NF-κB pathway in ~50% of ABC and ~20% of GCB DLBCL tumors is the presence of oncogenic mutations in CARD 11, TNFAIP3(A20), TNFRSF11A(RANK), TRAF2, TRAFS, MAP3K7(TAK1) and MYD88.

The differential engagement of the NF-κB pathways in ABC and GCB DLBCL observed in the disclosed gene expression analysis raises the possibility that each NF-κB pathway has specialized functions during B cell differentiation. This possibility is plausible based on key features of murine models lacking one of NF-κB subunits. Knockout NF-κB1 or NF-κB2 mice demonstrate impairment of the generation of mature B cells and Ig production, and in models lacking of IKK subunits, supports its involvement in early B cell development (1-chain positive pre-B cells). Furthermore, the central role of the interplay between the NF-κB pathways and regulators of B and plasma cell differentiation (BCL6 and BLIMP1, respectively) in the development of GCB and ABC DLBCL support this hypothesis. However, the intricate oncogenic interactions that promote the engagement of a particular NF-κB pathway during lymphomagenesis remain to be elucidated.

The specialized function of these pathways is further supported by the effect of rituximab on each NF-κB classifier. The finding that rituximab's effect converges on an inhibition of the genes included in the p105 classifier and a compensatory activation of p100 target genes provides an explanation for the selective regulation of this pathway and rituximab's recognized partial NF-κB inhibitory effect. Among its intracellular effects, rituximab prevents the complex formation of TAK/IKKa/IKKb necessary for activation of the canonical NF-κB pathway. However, the compensatory activation of the noncanonical NF-κB signaling pathway remains unexplained, and little is known about the capacity of RKIP to redirect the NF-κB activating signal towards the noncanonical NF-κB pathway.

The prominent difference in outcome after treatment with rituximab and DNA damaging agents observed between patients enriched for p100 and p105 target genes or in cells with or without NF-κB activation may also depend on the unique genomic regulatory effects executed by each signal. Given the prominent host inflammatory response in DLBCL, it is of interest that tumors enriched in p105 classifier express several genes that limit the effectiveness of host immune response (HLA-E, HLA-F, NCOA and C2). Recent reports suggest that HLA-F and HLA-E interact with the inhibitory counter-receptors, ILT2 and ILT4, potentially limiting associated T and NK cell response. The nuclear receptor coactivator 1 (NCOA), regulates the coactivation of STAT3 under IL6 stimulation. The second component of the complement (C2), a central component of the classical pathway of complement activation, can interfere with the binding of NK cells to immunoglobuling-coated targets. In addition, the p105 classifier includes genes with prosurvival functions like Ras association domain-containing protein 4 (RASSF4).

In the case of patients enriched for p100 classifier the lower overall benefit of rituximab may relate to its lack of inhibitory effect on this signal and the function of the genes included. The p100 gene classifier includes a number of genes involved in the regulation of mitosis and spindle formation: nucleoporin SEH1, protein Spindly (CCDC99), HAUS augmin-like complex subunit 6 (FAM29A), cyclin A2 (CCNA2), MAD2 mitotic arrest deficient-like 1 (MAD2L1), kinesin-like protein KIF11 and protein ECT2. A second large component includes genes involved in DNA repair: histone-lysine N-methyltransferase SETMAR1, ubiquitin specific peptidase 1 (USP1), protein MCM10 homolog (MCM10), PARP1-binding protein (C12orf48), lymphokine-activated killer T-cell-originated protein kinase (PBK), DNA mismatch repair protein Msh2 (MSH2) and dihydrofolate reductase (DHFR). A third group of genes is involved in RNA processing: 60S ribosome subunit biogenesis protein NIP7 homolog (NIP7), serine/arginine-rich splicing factor 3 (SFRS3), ribosome biogenesis protein BRX1 homolog (BRIX1) and eukaryotic translation initiation factor 4E (EIF4E). Overall, these findings indicate a specialized function of the noncanonical NF-κB pathway in maintaining genome integrity in B cells.

The multiple genetic alterations in DLBCL that result in dysregulation of the NF-κB signals will ultimately affect the expression of their target genes. Taking advantage of their downstream effects, the gene expression classifiers detailed in the present disclosure provide a convenient strategy to determine their functional transcriptional consequences. For example, the identification that DLBCL can now be segregated according to its transcriptional NF-κB pathway enrichment (p100 or p105) opens new avenues for identifying the role of each NF-κB pathway in the process of lymphomagenesis and tumor maintenance. Finally, this knowledge holds promise for screening novel biological agents directed at affecting downstream events associated with the regulation of a particular NF-κB pathway involved in disease development.

Measuring Activation of Genes Controlled by p105 and p100 Classifiers

In certain embodiments, the methodology for distinguishing samples with canonical (p105) or noncanonical (p100) NF-κB activation pathways using the p100 and p105 classifiers may involve microarray hybridization method of nucleic acids extracted from the samples and from control tissues with a predetermined gene expression pattern.

In certain embodiments, the methodology for distinguishing samples with canonical (p105) or noncanonical (p100) NF-κB activation pathways using the p100 and p105 classifiers may involve methods, devices, and kits routinely used in the art for detection of gene expression changes by detecting changes in genes' nucleic acid level. Such methods, devices, and kits may include nucleic acid hybridization, hybridization with reporter probes using nucleic acid or protein probes, such as antibodies, to specific gene sequences, in situ hybridization, Northern and Southern blotting, polymerase chain reaction (PCR), quantitative real-time PCR or quantitative real-time PCR with reporter probes such as oligonucleotide probes that contain a fluorophore attached to the 5'-end and a quencher at the 3'-end wherein the 5' to 3' exonuclease activity of the polymerase degrades the probe during PCR to producing a signal such as in TaqMan™ assays, PCR reporter assays for detecting activation or suppression of gene expression by detecting genes' promoter activity, hybridization with labeled micro-RNAs, barcoded oligonucleotide probes that hybridize directly to a target molecule in solution in combination with a capture probe that allows the complex to be immobilized for data collection such as in nCounter™ assays, to and variants thereof.

In certain embodiments, the methodology for distinguishing samples with canonical (p105) or noncanonical (p100) NF-κB activation pathways using the p100 and p105 classifiers may involve methods, devices, and kits routinely used in the art for detection of gene expression changes by detecting changes in genes' protein level. Such methods, devices, and kits may include enzyme linked immunosorbent assay (ELISA), Western blotting, pull-down with specific antibodies, pull-down with specific antibodies and Western blotting, mass spectrometry, protein activity assays using protein-specific ligands or substrates, and variants thereof.

In certain embodiments, the control tissues are the OCI-LY3 and Daudi cell lines expressing p100- or p105-short hairpin RNAs (shRNA). Raw data obtained from the microarray may first be log2-transformed and quantile normalized. Using a false discovery rate of 0.001 applied to P-values that are adjusted for multiple testing using the Benjamini-Hochberg method, a set of genes for which the expression levels were highly affected by the expression of p100- or p105-shRNA is compared to the expression levels of the same set of genes in the test sample. The full list of genes for which the expression levels were highly affected by the expression of p100- or p105-shRNA is presented in the NIH Gene Expression Omnibus data base at www.ncbi.nlm.nih.gov/geo under the accession number GSE24020. This analysis unveils two components in each target gene list: suppressed genes, genes in which the expression level increased during the expression of each NF-κB-shRNA and dependent genes, which contained genes downregulated by each NF-κB-shRNA expression.

In certain embodiments, selected probes of the genes contained in the p100 and p105 gene list may undergo a complete linkage agglomerative hierarchical clustering analysis to demonstrate two sets of pattern of expression specific to each pathway (training set) after the raw data is log 2-transformed and normalized using quantile methods. In certain other embodiments, a significance analysis of microarrays (SAM) in the training gene expression dataset may be performed to evaluate for genes with a robust capacity to predict pathway deregulation.

In certain embodiments, a complete linkage agglomerative hierarchical clustering analysis of the training dataset may be performed to evaluate the capacity of these classifiers to identify tumor samples enriched in p100 or p105 target genes. The gene list may then be filtered to exclude genes with probes that failed to cluster with the corresponding classifier.

In certain other embodiments, the methodology for distinguishing samples with canonical (p105) or noncanonical (p100) NF-κB activation pathways using the p100 and p105 classifiers may employ the nCounter Analysis System, provided by NanoString Technologies. In brief, to perform nCounter™ assay, 100 ng of total RNA or 2 μL of tissue lysate per replicate are used. The nCounter CodeSet for these studies may contain probe pairs for 47 test and 3 control genes. All 47 genes and controls (n=3) are assayed simultaneously in multiplexed reactions. Because the original 3 reference control genes may fluctuate significantly across experimental conditions, the slight differences in hybridization and purification efficiency can be accounted for by normalizing the log-2 data using quantile normalization. Subsequently, supervised complete linkage agglomerative hierarchical clustering analysis may be performed.

In certain other embodiments, the overall survival of patients treated with RCHOP or CHOP may be predicted and this prediction is based on the patients having samples with canonical (p105 classifier) or noncanonical (p100 classifier) NF-κB pathway activation. In certain embodiments, the overall survival may be estimated with Kaplan-Meier methods and log rank test for comparison of the survival between treatment groups. In certain embodiments, the different effect of pathway activation on clinical outcome may further be quantified as the ratio of the hazard ratios (HR) of the two groups of patients receiving different treatment (RCHOP vs CHOP) using COX proportional hazard model between the two strata of patients (pathway p100 vs p105) and tested using t-test with pooled variance.

In other embodiments, the disclosure may include devices for the use in the method for distinguishing samples with canonical (p105) or noncanonical (p100) NF-κB activation pathways using the p100 and p105 classifiers. Examples of such devices may include oligonucleotide arrays, such as microarrays, or equivalents thereof. In certain other embodiments, the disclosure may include kits comprising said devices, and solutions necessary to perform the analysis of gene expression patterns in said tissues.

EXAMPLES

Development of p100 and p105 Classifiers

Two lymphoma cell lines known to have NF-κB activation (Daudi and OCI-LY3) were used to identify genes particularly regulated by each NF-κB pathway. Using a lentivirus system, stable cell lines expressing a p100- and p105-shRNA (NF-κB-shRNA) were developed, thus inhibiting the downstream events of the noncanonical and canonical NF-κB pathway, respectively. Comparative gene expression analysis between NF-κB-shRNA and control-shRNA expressing cell lines identified a set of genes for which the expression levels were highly affected by p100- or p105-shRNA expression. This analysis revealed that each NF-κB's targeted gene list was comprised of two components: "dependent genes", genes under-expressed after NF-κB-shRNA expression, and "suppressed genes", genes overexpressed after NF-κB-shRNA expression. Subsequently, the p100 or p105 target genes from each cell line were combined for further processing.

Figure 1B:
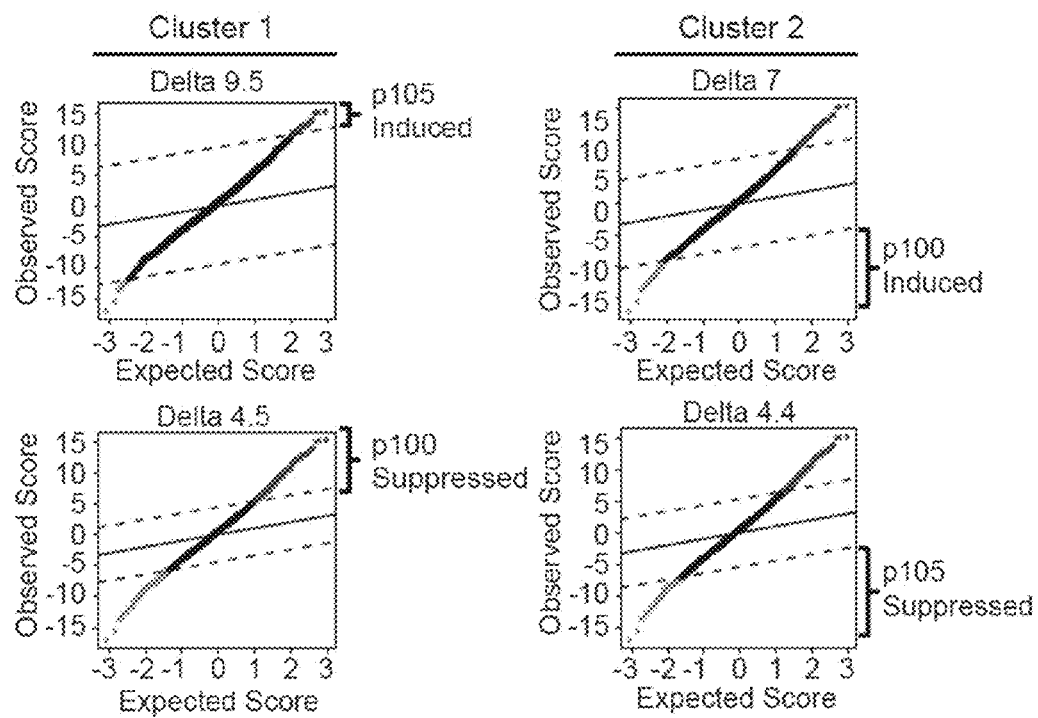
FIG. 1B illustrates significant analysis of microarrays (SAMr) analysis in a training dataset was performed using different delta values. A shortlist of 80 genes was detected to be highly segregated. Cluster 1 is p105 Classifiers and Cluster 2 is p100 Classifier.

To generate gene expression classifiers that reflect the activity of each NF-κB pathway, the identified canonical (p105) and noncanonical (p100) NF-κB gene list was used to perform hierarchical clustering analysis in a cohort of DLBCL samples included in microarray dataset (GSE4475). This analysis identified two groups of tumor samples with opposing patterns of gene expression between genes regulated by p100 and p105 (FIG. 1A). After selecting tumor samples enriched for the expression of p100 or p105 target genes (n=81), a significance analysis of microarrays (SAM) to identify genes highly changed in expression was performed. Using a false discovery rate of zero and different delta values, it was discovered that the p105 target gene classifier (n=39) was composed of genes dependent on p105 (n=21) and suppressed by p100 (n=18). In contrast, the p100 target gene classifier (n=41) was composed of genes dependent on p100 (n=16) and suppressed by p105 (n=25, FIG. 1B). To increase the clustering power of the p100 and p105 target gene classifiers, p100 and p105 target gene lists were applied in the training dataset to perform hierarchical clustering analysis. Genes found after filtering out from gene-probes that failed to cluster with the corresponding classifier were selected for further validation (FIG. 1C-D, and Table 1). This strategy identified 48 genes, equally distributed between the p100 and p105 classifiers.

TABLE 1

List of genes used in p105 and p100 classifiers

| Entrez Gene ID | Gene Symbol | Gene Title |
|---|---|---|
| 79444 | BIRC7 | baculoviral IAP repeat containing 7 |
| 55299 | BRIX1 | biogenesis of ribosomes, homolog (*S. cerevisiae*) |
| 55010 | C12orf48 | PARP1 binding protein |
| 717 | C2 | complement component 2 |
| 54908 | CCDC99 | coiled-coil domain containing 99 |
| 890 | CCNA2 | cyclin A2 |
| 1353 | COX11 | cytochrome c oxidase assembly homolog (yeast) |
| 22898 | DENND3 | DENN/MADD domain containing 3 |
| 1719 | DHFR | dihydrofolate reductase |
| 23234 | DNAJC9 | DnaJ (Hsp40) homolog, subfamily C, member 9 |
| 1894 | ECT2 | epithelial cell transforming sequence 2 oncogene |
| 1977 | EIF4E | eukaryotic translation initiation factor 4E |
| 54932 | EXD3 | exonuclease 3'-5' domain containing 3 |
| 54801 | FAM29A | HAUS augmin-like complex, subunit 6 |
| 79567 | FAM65A | family with sequence similarity 65, member A |
| 3133 | HLA-E | major histocompatibility complex, class I, E |

TABLE 1-continued

List of genes used in p105 and p100 classifiers

| Entrez Gene ID | Gene Symbol | Gene Title |
| --- | --- | --- |
| 3134 | HLA-F | major histocompatibility complex, class I, F |
| 3329 | HSPD1 | heat shock 60 kDa protein 1 (chaperonin) |
| 3383 | ICAM-1 | intercellular adhesion molecule 1 |
| 3726 | JUNB | jun B proto-oncogene |
| 3832 | KIF11 | kinesin family member 11 |
| 4000 | LMNA | lamin A/C |
| 4085 | MAD2L1 | MAD2 mitotic arrest deficient-like 1 (yeast) |
| 55388 | MCM10 | minichromosome maintenance complex component 10 |
| 4436 | MSH2 | mutS homolog 2, colon cancer, nonpolyposis type 1 (E. coli) |
| 8648 | NCOA1 | nuclear receptor coactivator 1 |
| 4779 | NFE2L1 | nuclear factor (erythroid-derived 2)-like 1 |
| 51388 | NIP7 | nuclear import 7 homolog (S. cerevisiae) |
| 55872 | PBK | PDZ binding kinase |
| 23129 | PLXND1 | plexin D1 |
| 5467 | PPARD | peroxisome proliferator-activated receptor delta |
| 83937 | RASSF4 | Ras association (RalGDS/AF-6) domain family member 4 |
| 81929 | SEH1L | SEH1-like (S. cerevisiae) |
| 6419 | SETMAR | SET domain and mariner transposase fusion gene |
| 6428 | SFRS3 | serine/arginine-rich splicing factor 3 |
| 11346 | SYNPO | synaptopodin |
| 84951 | TNS4 | tensin 4 |
| 7398 | USP1 | ubiquitin specific peptidase 1 |
| 60685 | ZFAND3 | zinc finger, AN1-type domain 3 |

Figures 2A, 2B:
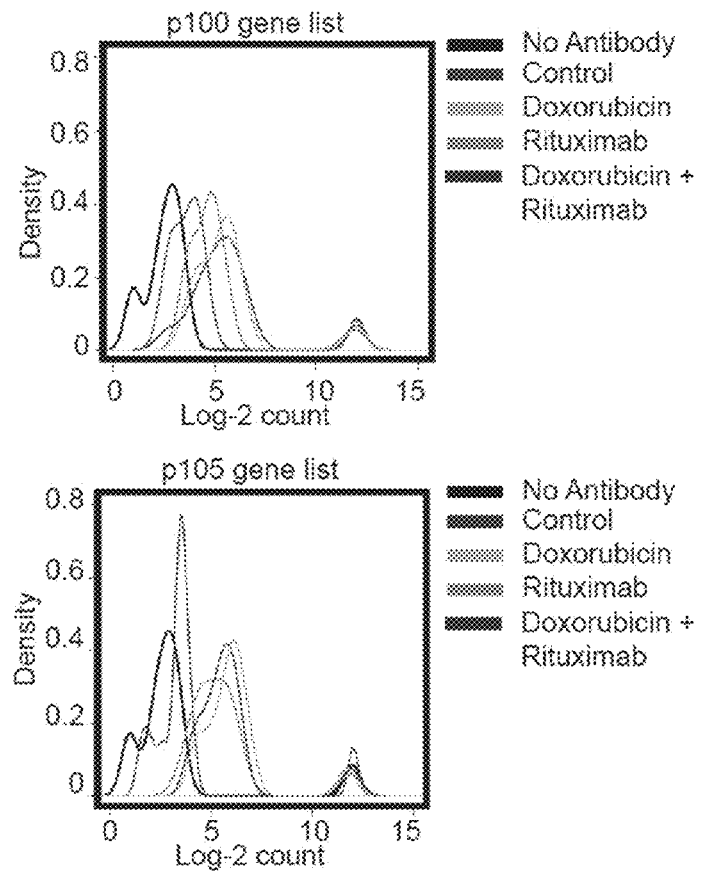
FIG. 2A illustrates the validation of the p100 and p105 classifiers in mouse models and primary tumor samples. Receiver operating characteristic (ROC) analysis used to estimate the predictive power of average of the average intensity (AI) ratio of Rel A/Rel B on detecting the pathway activation of the pathway identified by our gene classifier (area under the curve [AUC]=0.8677 and p-value [vs AUC=0.5]=0.0001).
FIG. 2B table summarizes different cutoff points for different sensitivities and specificities based on the Rel A/Rel B ratio and the overall percent of agreement between these two methods when a cut off of 1.105 was used.

To evaluate more formally the robustness of the pathway classifiers to accurately represent the status of activation of the canonical and noncanonical NF-κB pathways, the recruitment of the NF-κB subunits (p100 or p105) to the promoter kb binding regions of genes comprised in each classifier was investigated. To this end, OCI-LY3 cells before and after treatment for 1 hour with different drug combinations (doxorubicin, rituximab or doxorubicin and rituximab) were harvest to perform nCounter chromatin immunoprecipitation (CHIP) of multiple loci pull down by p100 or p105 antibodies. Density plots of log-2 transformed data of each experimental condition demonstrated that, when compared to the reference antibody, the kb binding site of nearly all genes loci physically interacted with their corresponding NF-κB regulatory subunit (FIG. 2A). To search for genes in which their transcription was directly influenced by p100 and p105 binding, an nCounter expression data obtained from OCI-LY3 cells was subjected to similar experimental conditions as the nCounter CHIP experiments. nCounter-CHIP assay analysis and correlation analysis with nCounter expression data was performed to identify which gene's functional NF-κB binding site enrichment display a high correlation with changes in gene expression and showed that the expression of certain components of the classifier highly correlated with the enrichment of their NF-κB subunit to the selected kb binding site (FIG. 2B, Table). This data also supported the notion that each pathway positively or negatively regulates the expression of their corresponding dependent or suppressed genes.

Figures 2C, 2D:
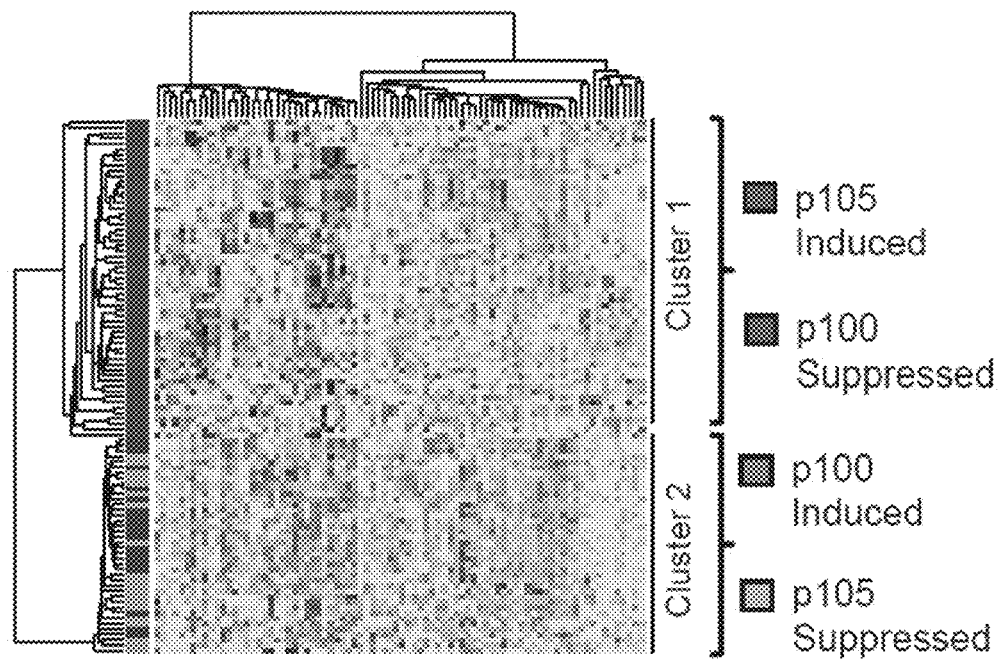
FIG. 2C provides a heatmap analysis of the complete DLBCL population included in GSE4475 dataset using the final p100 and p105 classifier gene lists. Coding of the side bar represents the type of regulation produced by each subunit (p100 or p105) per gene.
FIG. 2D is a table that lists the final components of the p100 and p105 classifiers obtained after performing hierarchical clustering analysis in the training dataset and filtering out genes with probes that did not follow their corresponding classifier.

Further verification of the capacity of oncogenic pathway signatures to predict accurately the status of pathways was also documented by the detection of Rel A and Rel B nuclear intensity (AI) in 39 primary tumor samples. To this end, a receiver operating characteristic curve to determine the capacity of Rel A/Rel B AI ratio in predicting the activation of the pathway detected by the gene classifiers was performed. As shown in FIG. 2B, the Rel A/Rel B AI ratio is significantly associated with the pathway detected by the gene classifier and it demonstrated significant predictive power for the pathway classifier (area under the curve [AUC]=0.8677 and p-value [vs AUC=0.5]=0.0001). In addition, the percent of agreement between the two methods of detection of activation of the NF-κB pathways was measured. FIG. 2C (table) summarizes different cutoff points for different sensitivities and specificities based on the Rel A/Rel B ratio, specifically, when a cut off of 1.105 was used the overall percent of agreement between these two methods maximize as 93%.

Figure 3A:
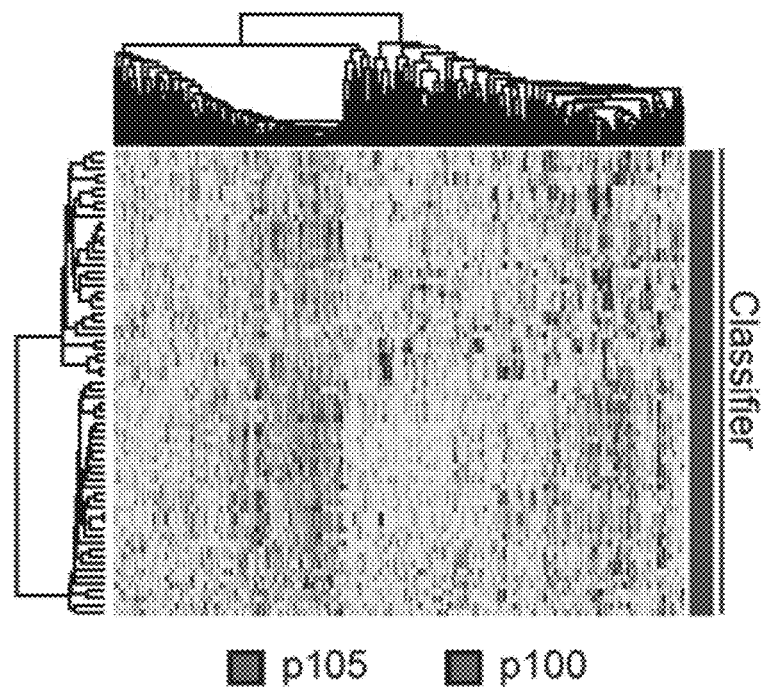
FIG. 3A illustrates the canonical and noncanonical pathway dysregulation within DLBCL. Hierarchical clustering analysis of p100 and p105 classifiers from 2 published datasets (complete group of DLBCL samples included in GSE4475
Figure 3B:
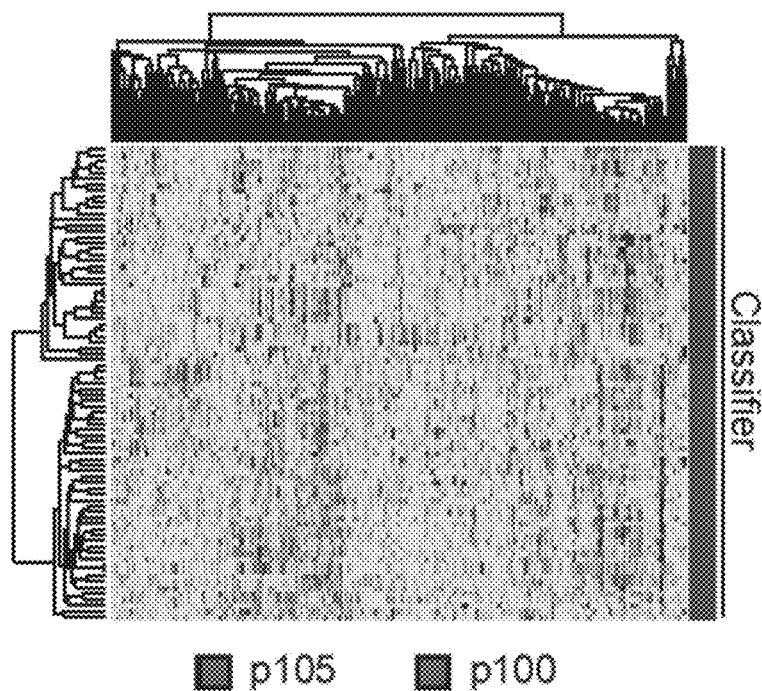
FIG. 3B shows data for published RCHOP-treated group included in GSE10846
Figure 3C:
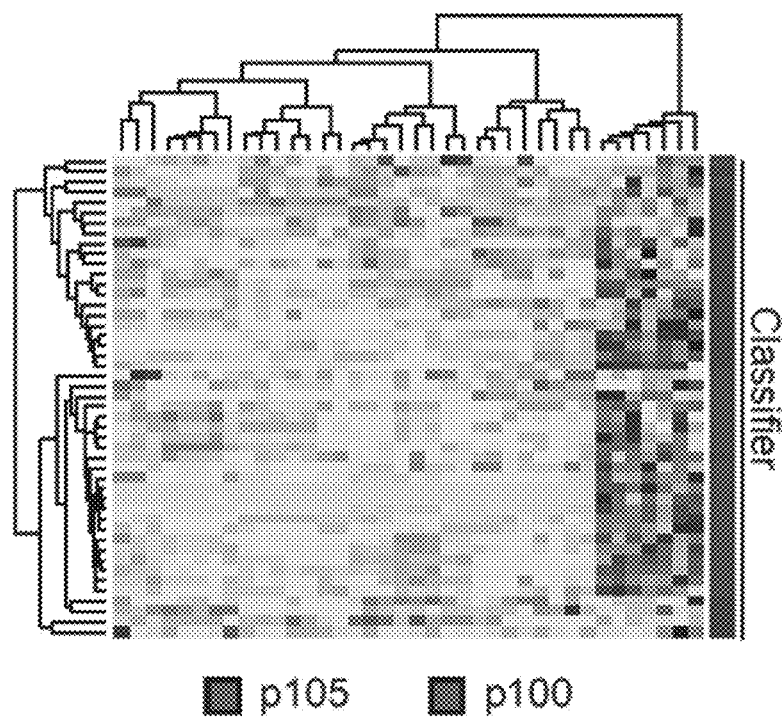
FIG. 3C shows data for an nCounter gene expression dataset of 39 patients.
Figure 3D:
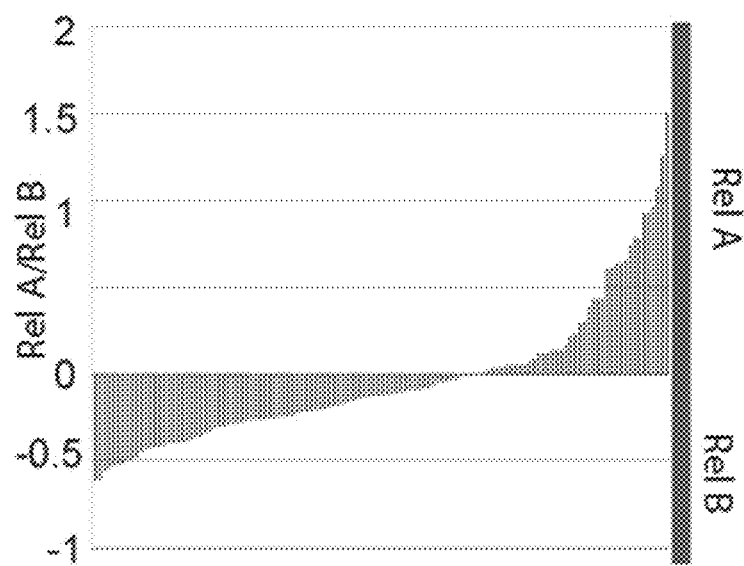
FIG. 3D shows data for Rel A (corresponding to p105 classifier) or Rel B (corresponding to p100 classifier) nuclear AI in 116 DLCBCL tumor samples.

Differential Activation of the Canonical and Noncanonical NF-κB Pathway within DLBCL The capacity to perform pathway analysis by both methods gives the ability to identify patterns of pathway dysregulation within DLBCL samples. Three additional validation experiments made use of two of the largest published gene expression and clinically annotated dataset of DLBCL samples (GSE4475 and GSE10846) and an nCounter gene expression dataset of 39 patients (FIG. 3A-C). In all datasets, the NF-κB classifiers segregated DLBCL into two major groups according to their p100 and p105 transcriptional profile: p100 and p105 target enriched patients. These results were substantiated by detecting Rel A (corresponding to p105 classifier) or Rel B (corresponding to p100 classifier) nuclear AI in 127 tumor samples. This strategy identified that Rel A or Rel B were localized in the nucleus of almost all tumor samples, and consistent with the gene expression analysis, two major groups of NF-κB activated tumor samples were identified (FIG. 3D).

To comprehensively discover the difference between the designed NF-κB classifiers and a previously reported NF-κB signature, unsupervised hierarchical clustering analysis in two different datasets was performed. Notably, the p105 classifier clustered consistently with the previously published NF-κB signature, suggesting that this signature represents the status of activation of the canonical NF-κB pathway. However, the p100 classifier detected a high transcriptional activity of the noncanonical pathway in the remaining large fraction of DLBCL cases.

Figures 4A, 4B:
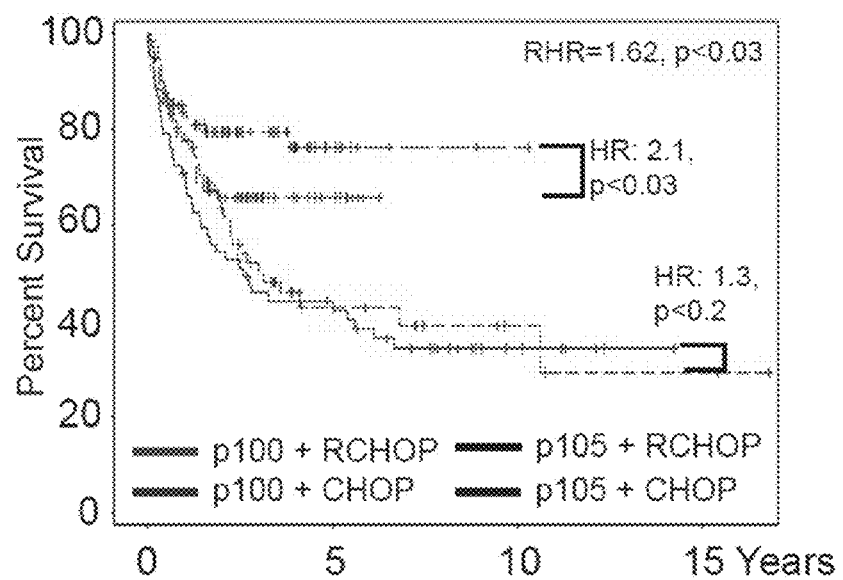
FIG. 4A illustrates the effect of the canonical and noncanonical NF-κB pathways on overall survival (OS) and tumor type. Multivarible analysis in patients with tumors enriched for p100 or p105 classifiers included in GSE10846. Survival analysis using COX model after adjusting for the gender, age, stage, and ECOG performance status; and after adjusting for DLBCL subtype.
FIG. 4B shows Kaplan-Meier curves of patients with tumors enriched for p100 and p105 target genes according to the treatment received (RCHOP or cyclophosphamide, doxorubicin hydrochloride (hydroxydaunorubicin), vincristine sulfate (Oncovin), and prednisone (CHOP) alone). OS was estimated with Kaplan-Meier methods and log rank test was used for comparison of the survival between treatment groups.

Status of Activation of the Canonical and Noncanonical NF-κB Pathway Predicts Overall Survival in RCHOP-Treated Patients While the analysis of gene expression shown in FIG. 3 depicts the status of activation of both NF-κB pathways among different DLBCL cases, the importance of these approaches is the ability to delineate the importance of activation of NF-κB pathway in clinical outcome. To this end, multivariable analysis in patients with tumors enriched for p100 or p105 target genes included in a cohort of patients treated with CHOP and RCHOP (GSE10846) was performed. After adjusting for gender, age, stage, and ECOG, a significant difference in overall survival (OS) between patients enriched for p100 or p105 target genes (FIG. 4A) was found. Furthermore, the effect of pathway activation on OS remained present when the analysis was adjusted for the therapeutic regimen used. No significant interaction was demonstrated between the therapy type and the pathway activated (p=0.5908). However, when the analysis was adjusted for DLBCL subtype, the effect of the NF-κB pathways in OS disappeared, suggesting that there is a substantial overlap in the effect on OS between the pathway activation and DLBCL subtype (FIG. 4A-B). Similar analysis was performed on the DLBCL cases included in the GSE4475 dataset and these significant findings failed to reproduce. This difference probably reflects the small number of patients treated with CHOP (n=53) or RCHOP (n=10)

and the lower number of patients with ABC DLBCL subtype included in GSE4475 (ABC=20 and GCB=32).

Figures 4C, 4D:
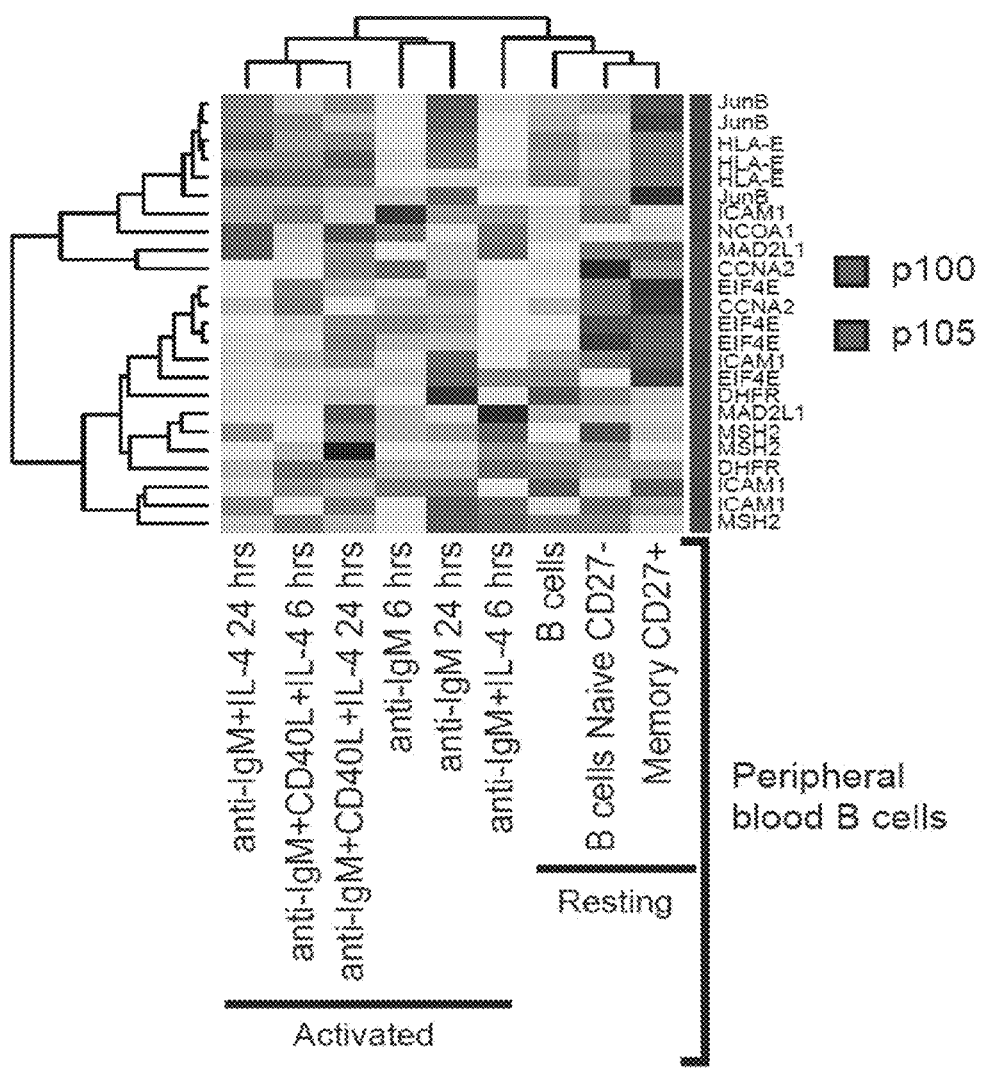
FIG. 4C shows Rel A or Rel B nuclear AI in 72 DLBCL biopsies immunohistochemically classified as germinal center B cell-like (GCB) or nonGCB based on the Hans algorithm (NGC=37 and GCB=46) and normal tonsillar tissue (n=20).
FIG. 4D shows a hierarchical clustering analysis demonstrated that resting B cells predominantly express genes within the p105 classifier, while in activated B cells the expression shift towards genes within the p100 classifier.

To explore the ability of both NF-κB classifiers to delineate clinically relevant subsets of DLBCL and their clinical outcome, the hazard ratios for the pathways-enriched populations (p100 and p105) between patients treated with RCHOP and CHOP were compared. As shown in FIG. 4C and Table 2, the ratio of the hazard ratio for both pathways between patients treated with CHOP and RCHOP was 1.62 (95% confidence interval (CI):1.037, 2.537), suggesting that the better OS obtained by adding rituximab to CHOP was significantly more obvious in p105 than p100 enriched patients (p=0.0339).

Link Between p100 or p105 Enrichment and Tumor Subtype and Other Molecular Events Previous work linked ABC DLBCL subtype with worse survival and with NF-κB activating mutations. To investigate whether one of the NF-κB pathways is predominantly engaged in certain DLBCL subtypes, a multivariable analysis in the largest DLBCL dataset (GSE10846) was performed. It was found that within each group of patients stratified by the therapeutic regimen, ABC DLBCL was significantly more likely to be associated with p100 enrichment and GCB DLBCL was more likely to be associated with p105 enrichment (FIG. 4E). The differential activation of the NF-κB pathways according to the B cell subtype was further validated using a published dataset (GSE60) that measured the transcriptional change of B cells after activation with immunoglobulin M (IgM)±interleukin 4 (IL-4) ±cluster differentiation 40L (CD4OL). Using the common genes between the classifiers and this dataset, a hierarchical clustering analysis was performed and demonstrated that resting B cells predominantly express genes within the p105 classifier, while in activated B cells the expression shift towards genes within the p100 classifier (FIG. 4F). Engagement of the canonical and noncanonical NF-κB pathways was also documented by evaluating Rel A or Rel B nuclear AI in 72 DLBCL biopsies immunohistochemically classified as GC or nonGCB based on the Hans algorithm (NGC=37, GCB=46 and normal tonsillar tissue=20). The nuclear AI of Rel A was higher in GCB than ABC DLBCL, although it was not statistically significant. However, both DLBCL subtypes nuclear intensities were significantly higher with respect to normal centroblast obtained from tonsil tissues.

In addition to the association between DLBCL subtype and activation of one of the NF-κB pathways, the patterns of pathway activation and other intrinsic molecular events available in the dataset GSE4475 were explored. This analysis identified that p100-enriched tumors were more frequently associated with a high Burkitt's lymphoma probability and higher levels of Ki67. Instead, p105-enriched tumors were predominantly associated with Bcl-6 breaks, Bcl-2 expression and IgH-Bcl-2 fusion. These results provide insight into the nature of the NF-κB pathway association across the different molecular events that affect clinical outcome.

Figure 5A:
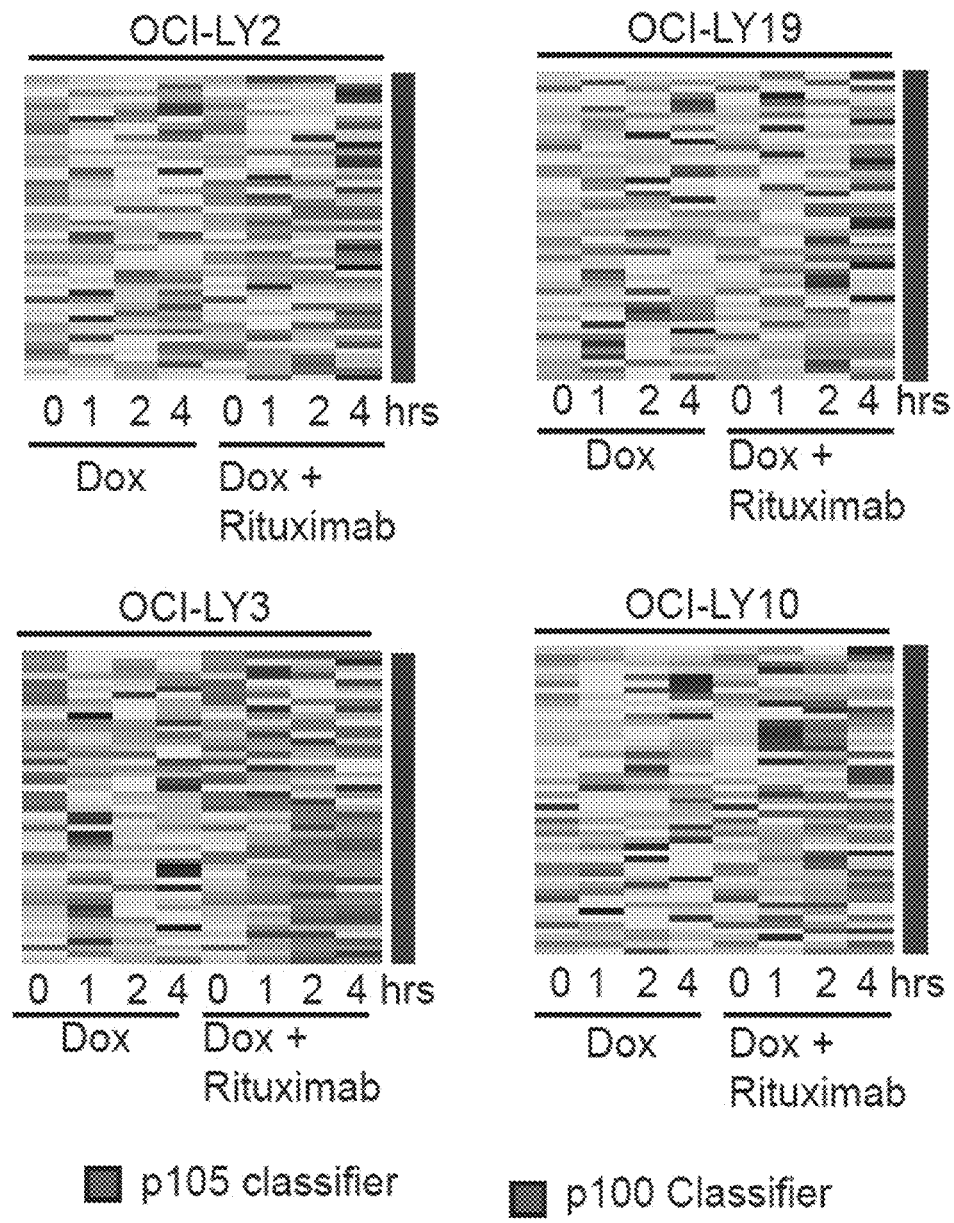
FIG. 5A illustrates that rituximab increases the apoptotic effect of doxorubicin when it is associated with suppression of p105 and induction of p100 classifier gene expression. Boxplot of p100 and p105 gene list illustrating the changes in gene expression in cells treated with doxorubicin (2mg/mL) or rituximab (10 mM/mL). Cells were treated for 24 hours and the percent of live cells was measured using an ImageXpress 5000A Automated Acquisition and Analysis System (Molecular Devices), quantitating for Yo-pro-1 or PI-negative cells.
Figure 5B:
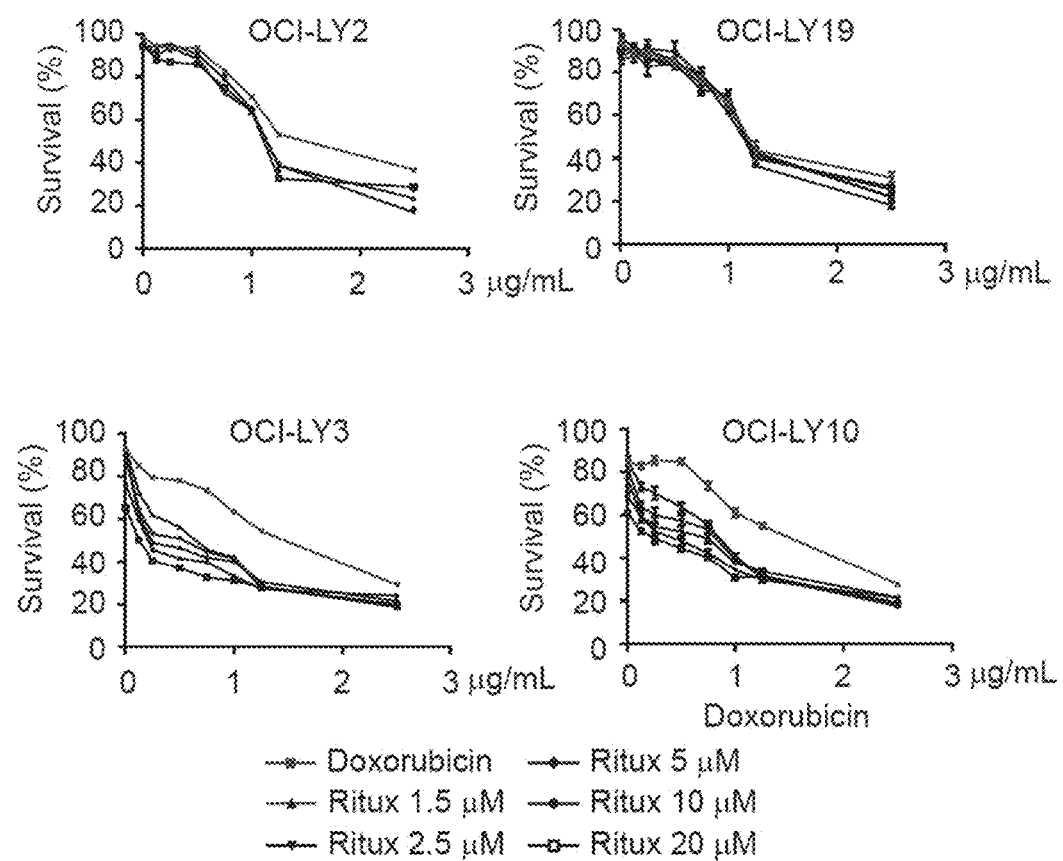
FIG. 5B illustrates Supervised hierarchical clustering analysis illustrates the individual gene changes during treatment (right panel). Treatment curves of titrating doses of doxorubicin or doxorubicin combined with rituximab.

Rituximab Exclusively Suppresses the Expression of p105 Target Genes and Induces p100 Target Genes Given the capacity of the p105 classifier to predict a better response to RCHOP, the extent to which both classifiers were targeted by rituximab was investigated. In this investigation, the pathway dysregulation in a series of DLBCL cell lines and their changes in gene expression produced by DNA damaging agent (doxorubicin) and rituximab was measured. Based on their known baseline pattern of NF-κB activation, cell lines with enhanced (OCI-LY3, OCI-LY10) and suppressed (OCI-LY19 and OCI-LY2) NF-κB activation were selected for further testing (FIG. 5A). As shown in FIG. 5B, doxorubicin moderately induced the gene expression of p100 and p105 target genes in OCI-LY3, OCI-LY10 cells. Notably in NF-κB activated cell lines, rituximab suppressed doxorubicin's induction of p105 gene classifier while it enhanced the induction of p100 gene classifier, providing strong evidence for the canonical NF-κB pathway (p105 classifier) being the target for rituximab.

To assess the consequence of rituximab's functional effects, the degree of apoptosis produced after treating all four cell lines with titrating doses of doxorubicin and rituximab was measured. Rituximab alone did not induce significant apoptosis beyond background levels in all cell lines. Similarly, cell lines (OCI-LY2 and OCI-LY19) in which rituximab minimally changed the expression of p100 and p105 classifiers showed no increase in apoptosis when rituximab was combined to doxorubicin. In contrast, cell lines in which rituximab suppressed p105 classifier gene expression demonstrated a higher sensitivity to doxorubicin-rituximab combination. Together these data suggest that rituximab's functional effects on cells with an activated canonical NF-κB pathway are important for restoring the apoptotic sensitivity to doxorubicin.

Cell Lines and RNA Preparation

Burkitt lymphoma Daudi cell line was grown in RPMI medium supplemented with 10% fetal bovine serum, 1% L-glutamine, 1 mM sodium pyruvate, and 50 µg/ml penicillin-streptomycin. The ABC DLBCL cell line, OCI-LY10 and OCI-LY3, and GCB DLBCL cell lines, OCI-LY2 and OCI-LY19, were maintained in Iscove's medium supplemented with 20% fresh human plasma (Innovative Research), 1% L-glutamine, 1 mM sodium pyruvate, and 50 µg/ml penicillin-streptomycin. The HEK 293 cell line was maintained in Dulbecco's modified eagle medium with 10% fetal bovine serum, 1% L-glutamine, 1 mM sodium pyruvate, and 50 µg/ml penicillin-streptomycin.

Plasmids

RNA interference hairpins were expressed under the control of the U6 human promoter and were generated by using PLKopuro.1 (provided by S. Stewart, Washington University). Complementary shRNA oligos were annealed and cloned into vectors digested with AgeI and EcoRI and confirmed by sequence analysis. The sequence of the sense shRNA oligonucleotide probes were as follows: p105: CCT-TCCGCAAACTCAGCTTTA (SEQ ID NO: 1), p100: GCT-GCTAAATGCTGCTCAGAA (SEQ ID NO: 2), Rel A: CGGATTGAGGAGAAACGTAAA (SEQ ID NO: 3) and Rel B: AGCCCGTCTATGACAAGAAAT (SEQ ID NO: 4). Luciferase shRNA plasmid was kindly provided by S. Stewart.

Apoptosis Studies

For apoptosis studies, $10^4$ cells were treated with titrating doses of doxorubicin (titrating doses: 0.15, 0.25, 0.5, 0.750, 1, 1.5 and 2.5 mg/mL, Sigma) or rituximab (titrating doses: 1.5, 2.5, 5, 10 and 20 mg/mL, Biogen Idec Inc). Twenty four hours later cells were stained with Yo-pro-1 iodide and propidium Iodide (PI, both from Invitrogen). Live cells were measured using an ImageXpress 5000A Automated Acquisition and Analysis System (Molecular Devices), quantitating for Yo-pro-1 iodide and PI negative cells.

Immunoblotting and Nuclear Extraction

Cells were lysed with cell lysis buffer (50mM Tris-Cl, pH 8, 5mM EDTA, 100mM NaCl, 0.5% Triton X-100 and protease and phosphatase inhibitors). The following antibodies were used: p100 (sc-7386), p105 (sc-7178), Rel A (sc-372), Rel B (sc-226), glyceraldehyde 3 phosphate dehydrogenase (GAPDH, sc-137179), all from Santa Cruz Biotechnology.

Immunofluorescence Studies

One hundred and twenty seven retrospective DLBCL samples were obtained from the institutional review board-approved hematology tissue acquisition and procurement bank program at Stanford University and Emory University Schools of Medicine. Three independent pathologists confirmed the pathological diagnosis of all samples and sub-classified DLBCL samples (n=72) between nonGCB and GCB using the Hans' protocol. One hundred and twenty seven 0.5-mm cores from diagnostic areas of each DLBCL sample were used to generate a single-recipient paraffin block using a tissue arrayer (Beecher Instruments, Silver Spring, Md.).

To validate the specificity of Rel A (sc-372, Santa Cruz, Bio) and Rel B (sc-226, Santa Cruz, Bio) antibodies before performing immunofluorescence (IF) in primary tissues, immunofluorescence analysis for Rel A and Rel B in Rel A or Rel B shRNA OCI-LY3 expressing cells was performed. After validating the antibodies specificity, five-micron sections of the tissue microarray were deparaffinized by incubating in an 80° C. water bath three times for 20-minutes followed by three 5-minute incubations in xylene and a series of ethanol solutions (100%, 90%, 75% and 50%). After washing with distilled water, antigen retrieval was performed by immersing the slides in a microwave solution (9 ml of 0.01M citric acid, 41 ml of 0.01 mM sodium citrate and 450 ml of water) and microwaving at low power three times for 5-minutes. Slides were pre-treated with blocking solution (10% goat serum/3% BSA/0.5% gelatin/PBS) for 1 hour to block non-specific binding sites. Primary antibodies for Rel A (sc-372) and Rel B (sc-226) were applied at 1:250 dilutions in 50 mM Tris-Cl (pH 7.4) with 3% goat serum overnight. After washing, secondary Alexa Fluor 488-conjugated antibodies (Molecular Probes) were applied for 1 hour. After further washing, slides were counter stained with 4, 6-diamidino-2-phenylindole (DAPI) for nuclear detection.

Image Acquisition and Nuclear Localization Quantification and Analysis

Images were acquired using a Zeiss LSM 510 META point scanning laser confocal microscope and captured by Zeiss Image LSM Browser (cell imaging and microscopy shared resource, Winship Cancer Institute of Emory University). Four images per sample were acquired in fields with a minimum of 200 cells. Quantification of the nuclear localization of Rel A and Rel B was obtained after performing a z-projection from the confocal microscope images and transforming them into grayscale. The resulting images were processed using Metamorph software (Universal Imaging Corporation). Briefly, image processing started with sharpening and selecting the nuclear image (DAPI) based on size, allowing the avoidance of large clumps and small debris. Each nucleus was used to create an object mask image, that was then dilated twice (2× dilate). The 2× dilate image was subtracted from the original nuclear mask leaving 2 images: nuclear mask and cytoplasmic mask arithmetic. Subsequently, both masks were applied to the image containing the staining for the protein of interest. The threshold for the image was selected for each staining group (Rel A and Rel B) to identify non-zero pixels. Measurements were then performed by obtaining the average intensity.

Statistical analysis for correlation between Rel A and Rel B was performed using the following defined measurement of the overall (among individual images) average of the average intensity (AI) for each tissue:

$$AI = \frac{\sum_{i=1}^{4} U_{j,i} * C_{j,i}}{\sum_{i=1}^{4} c_{j,i}}$$

where AI is the average of the average intensity per tissue, j is the sample, i is the image, u is the average intensity value and c is cell count.

Gene Expression and Statistical Analysis

Based on the well documented constitutive activation of NF-κB in OCI-LY3 and Daudi cells, gene expression data analysis on OCI-LY3 and Daudi cells expressing p105-, p100-, and Luc-shRNA was performed. Daudi and OCI-LY3 were infected for 48 hours with lentivirus expressing p100-, p105- or luciferase-shRNA when indicated. After two weeks of selection, confirmation of the knockdown of p100 and p105 was performed. At that time, triplicate samples of each shRNA-expressing cell line were used for comparative gene expression analysis. RNA samples were extracted from $50\times10^6$ cells using a Qiashredder and Qiagen RNeasy Mini kit (Qiagen) following the manufacturer's protocol. Quality of the RNA was checked by an Agilent 2100 Bioanalyser.

The methodology used to identify the full p100 and p105 targeted gene list has been previously described. In brief, microarray hybridization data was prepared by Cogenics, Inc, using an Agilent 4X44 platform. Scanning and image analysis were performed using an Agilent 2100 Bioanalyzer and Agilent MR-2 DNA Microarray Scanner (Agilent Technologies, Inc). Raw data were first log 2-transformed and quantile normalized. Using a false discovery rate of 0.001 applied to P-values that were adjusted for multiple testing using the Benjamini-Hochberg method, a set of genes was selected for which the expression levels was highly affected by the expression of p100- or p105-shRNA compared to cells expressing luciferase-shRNA to create a p100 and a p105 target gene list in each cell line. The gene lists obtained from OCI-LY3 and Daudi cell lines were subsequently combined to generate a share p100 or p105 target gene list. This analysis unveiled two components in each target gene list: Suppressed genes, genes in which the expression level increased during the expression of each NF-κB-shRNA and dependent genes, which contained genes downregulated by each NF-κB-shRNA expression. The microarray data analyzed in this study have been previously deposited in the NIH Gene Expression Omnibus database at www.ncbi.nlm.nih.gov/geo under the accession number GSE24020.

To generate gene expression classifiers that reflect the activity of the canonical or noncanonical NF-κB pathways, raw gene expression data of a cohort DLBCL patients included in a previously reported microarray dataset (GSE4475) was used. After the raw data was log2-transformed and normalized using quantile methods, probes of the genes contained in the p100 and p105 gene lists were selected. Complete linkage agglomerative hierarchical clustering analysis demonstrated two sets of tumors with a pattern of expression specific to each pathway (training set). To evaluate for genes with a robust capacity to predict pathway deregulation a significance analysis of microarrays (SAM) was performed in the training gene expression dataset. Different delta values (genes suppressed by p100: 7 and p105: 4.5 and dependent of p105: 9.5 and p100: 7, FIG.

1B) and a false discovery rate of zero yielded 80 significant genes. To evaluate the capacity of these classifiers to identify tumor samples enriched in p100 or p105 target genes, complete linkage agglomerative hierarchical clustering analysis of the training DLBCL microarray training dataset was performed. The gene list was then filtered to exclude genes with probes that failed to cluster with the corresponding classifier, leaving a final list of 48 genes equally distributed between p100 and p105 classifiers.

To evaluate the predictive validity and robustness of both classifiers to identify patient enriched for p100 or p105 target genes, both gene lists were applied to previously published gene expression datasets (GSE10846 and the complete population of DLBCL cases included in GSE4475) and a NanoString nCounter expression dataset of 39 cases. Raw data in all datasets were preprocessed by performing loge-transformation and normalized, using quantile methods, before carrying out supervised complete linkage agglomerative hierarchical clustering analysis.

The nCounter™ System Assay nCounter Analysis System technology was developed by NanoString Technologies. In brief, nCounter™ assay was performed using 100 ng of total RNA or 2 µL of tissue lysate per replicate. The nCounter CodeSet for these studies contained probe pairs for 47 test and 3 control genes. All 47 genes and controls (n=3) were assayed simultaneously in multiplexed reactions. Because the original 3 reference control genes fluctuated significantly across experimental conditions, slight differences in hybridization and purification efficiency were accounted for by normalizing the log-2 data using quantile normalization. Subsequently, supervised complete linkage agglomerative hierarchical clustering analysis was performed.

Agreement Between nCounter Expression Data and AI Rel A and Rel B Nuclear Intensity The nCounter expression data of p100 and p105 classifiers and the AI of Rel A and Rel B was determined in 39 tumor samples as described above. Activation of the pathway detected by the gene classifier was used as the gold standard. A receiver operating characteristic (ROC) analysis was performed to estimate the predictive power of AI ratio of Rel A/rel B to detect the status of activation identified by the gene classifier. An optimal cutoff point for the AI ratio of Rel A/rel B was estimated to maximize the sum of its sensitivity and specificity for detecting activation of each NF-κB pathway. Agreement between the two methods was measured as followed:

$$\frac{N1 \times Sen + N2 \times Spec}{N}$$

where N1 is the total number of p105 samples and N2 is the total number of p100 samples according to our gene classifier, N is the total number of samples analyzed, Sen is the sensitivity and Spec is the specificity.

The nCounter™ System CHIP Assay

Fifty million OCI-LY3 cells were harvested prior and after 60 minutes of treatment with doxorubicin alone or in combination with rituximab, fixed with 1.1% formaldehyde and quenched with 0.125M glycine. Chromatin was isolated by sequentially adding 3 different lysis buffers (LB1: 50mM Hepes-KOH, pH 7.5, 140mM NaCl, 1 mM EDTA, 10% Glycerol, 0.5% NP-40, 0.25% Triton X-100, LB2: 10 mM Tris-HCl, pH 8.0, 200 mM NaCl, 1 mM EDTA, pH 8.0, 0.5 mM EGTA, pH 8.0 and LB3: 10 mM Tris-HCl, pH 8.0, 200 mM NaCl, 1 mM EDTA, pH 8.0, 0.5 mM EGTA, pH 8.0, 0.1% Na-Deoxycholate, 0.5% N-lauroylsarcosine) followed by disruption with a dounce homogenizer. Using a Brandon sonifier cell disrupter 205 output setting of 3 and constant power (Branson Ultrasonics, CT), lysates were sheared under cold conditions to an average length of 300-500 bp. An aliquot of chromatin (30 mg) was precleared with protein A agarose beads (Invitrogen). Genes within the classifiers with kb binding sites in the promoter region were isolated from the genomic DNA using an antibody against p105/p50 (Abcam, ab7971) or p100/p52 (Abeam, ab7972). Following incubation at 4° C. overnight, protein A agarose beads were used to isolate the immune complexes. Complexes were washed, eluted from the beads with a 1% SDS/50 nM Tris/10 mM EDTA buffer, and subjected to RNase and proteinase K treatment. The antibody/chromatin complexes were reversed by incubation overnight at 65° C., and CHIP DNA was purified by phenol-chloroform extraction and ethanol precipitation. Length of the genomic DNA was evaluated using Micro-Volume UV-Vis Spectrophotometer (NanoDrop 2000, Termo Scientific, DE).

To measure enriched binding at each gene loci, a newly described CHIP-string method was used. To leverage on the nCounter analysis system platform, a probe set containing the kb binding site for each loci complementary to the genes contained on the classifiers was selected, when available. Quantification of DNA molecules by nCounter Analysis System was performed by Nanostring technology.

nCounter-CHIP Assay Analysis nCounter-ChIP data (CHIPstring) provided digital counts for each probe (rows) across all experiments (no treatment or 1 hour treatment with either rituximab, doxorubicin, or the combination of doxorubicin and rituximab). The two technical replicates of the reference sample (IgG control, "Mock") were used to calculate an average value and we assumed this to be our reference to estimate enrichment across p105 and p100 conditions. Counts were log-2 transformed to reduce the effect of extreme outliers in the dataset. The resulting log2-data of the genes selected as regulated by p100 or p105 (both dependent and suppressed) were used to generate empirical distributions.

Correlation of nCounter CHIP and Expression Data

To evaluate whether transcriptional regulation of the genes contained in each classifier is the result of direct binding of p100 or p105 to their respective promoters, expression data obtained from OCI-LY3 cells treated as described above and nCounter CHIP were used. Based on the changes in gene expression observed under different experimental conditions, the genes in which the enrichment of p100 or p105 was comparable to changes in gene expression were determined. This was accomplished by first taking the ratio of the p105 CHIP condition raw data to the p100 CHIP condition raw data, as well as the ratio of p100 CHIP data to the p105 CHIP data. These ratios were log-2 transformed and quantile normalized. For these ratios, the expected relationship among conditions for each p100 gene was: control<Dox1<DR1, and for each p105 gene was: control<DR1<Dox1, where Dox1 is cells treated with doxorubicin for 1 hour, DR1 is cells treated with the combination of doxorubicin and rituximab for 1 hour, and control is no treatment. For p105 dependent genes and p100 suppressed genes, it was expected that the gene expression values decrease from Dox1 to DR1; for p100 dependent and p105 suppressed genes, the gene expression values should increase from Dox1 to DR1. Thus, the binding for the ratio of p105/p100 for p105 dependent genes should mirror the direction of the p105 gene expression data. Likewise, the binding for the ratio of p100/p105 for p100 dependent genes should mirror the direction of the p100 gene expression data. The inverse relationship should be observed for suppressed genes. To assess the correlation between nCounter CHIP and nCounter Expression counts in each gene, conditions (control, dox1, and DR1) and genes common to both datasets were selected, and Pearson's correlation coefficient between the CHIP ratio and expression nCounter values for each gene was calculated. For p105 genes, the ratio of p105/p100 was used, and for p100 genes the p100/p105 ratio was used. Genes with a correlation value>+/−0.5 were defined as genes whose kb binding site is highly involved in gene expression regulation.

To assess the correlation between NF-κB enrichment and the expression in each gene, the correlation between nCounter CHIP and nCounter Expression counts was calculated. To this end the raw nCounter CHIP values of the reference sample were first subtracted from the other experimental conditions. In the resulting values, any sample less than or equal to 1 was set to 1. Because, it is unknown whether the selected kb binding regions are specific to a particular NF-κB subunit, a ratio of loci enrichment values between p100 to p105 CHIP samples or vice versa was generated. These ratios were log-2 transformed and quantile normalized. To assess the correlation between nCounter CHIP and nCounter Expression counts in each gene, common experimental conditions (control, dox1, and DR1) and genes between both datasets were selected. Pearson's correlation coefficient was then calculated. In this analysis, gene expression values of p105 dependent genes and p100 suppressed genes should decrease from Dox1 to DR1. In contrast, gene expression values of p100 dependent and p105 suppressed genes should increase from Dox1 to DR1. Thus, the binding for the ratio of p105/p100 for p105 dependent genes should mirror the direction of the p105 gene expression data. Likewise, the binding for the ratio of p100/p105 for p100 dependent genes should mirror the direction of the p100 gene expression data. Any inverse relationship should then be observed for suppressed genes. In this analysis, a correlation value>+/−0.5 defined genes whose kb binding site was highly involved in gene expression regulation.

Survival Analysis

Using the groups of patients with canonical (p105 classifier) or noncanonical (p100 classifier) NF-κB pathway activation identified in the GSE10846 data set, the overall survival of patients treated with RCHOP or CHOP was measured. Overall survival was estimated with Kaplan-Meier methods and log rank test was used for comparison of the survival between treatment groups. The different effect of pathway activation on clinical outcome was further quantified as the ratio of the hazard ratios (HR) of the two groups of patients receiving different treatment (RCHOP vs CHOP) using COX proportional hazard model between the two strata of patients (pathway p100 vs p105) and tested using t-test with pooled variance.

Analysis Software

For a significance analysis of microarrays and nCounter gene expression data, the statistical software R and the related BioConductor function packages were used. To identify genes with variable gene expression in the cell line experiments that generated the p100 and p105 gene lists, linear modeling approaches and empirical bayes statistics (limma package) were used.

Patient gene expression profiles were normalized using quantile normalization methods. P100 and p105 classifiers were generated by performing SAM, using SAMr package. Heatmap analysis with dendrograms and complete linkage agglomerative hierarchical clustering analysis were performed using the Made4 package. Kaplan-Meier mortality curves for survival analysis was measured using Graphpad Prims software.

What is claimed is:

1. A method of diagnosing and treating lymphoma comprising:

measuring in a lymphoma cell of a subject an increased RNA expression of HLA-F, HLA-E, ICAM-1, ZFAND3, LMNA, FAM65A, BIRC7, EXD3, SYNPO, TNS4 and a decreased RNA expression of NFE2L, NCOA1, JUNB, RASSF4, C2, PLXND1, DENND3, and PPARD compared to a non-tumor cell;

diagnosing the subject with a canonical NF-κB activation pattern; and administering an effective amount of rituximab, cyclophosphamide, hydroxydaunorubicin, vincristine, and prednisone to the subject in need thereof.

2. A method of diagnosing and treating lymphoma comprising:

measuring in a lymphoma cell of a subject an increased RNA expression of EIP4E, HSPD1, SFRS3, COX11, SEH1L, SETMAR, NIP7 and a decreased RNA expression of USP1, DNAJC9, CCDC99, FAM29A, MCM10, C 12orf48, PBK, MSH2, DHFR, CCNA2, MAD2L1, KIF11, and ECT2 compared to a non-tumor cell;

diagnosing the subject with a non-canonical NF-κB activation pattern; and administering an effective amount of rituximab, cyclophosphamide, hydroxydaunorubicin, vincristine, prednisone, and another anticancer agent to the subject in need thereof.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
ccttccgcaa actcagcttt a                                              21

<210> SEQ ID NO 2
<211> LENGTH: 21
<212> TYPE: DNA
<213> ORGANISM: Artificial
<220> FEATURE:
<223> OTHER INFORMATION: Synthetic

<400> SEQUENCE: 2
gctgctaaat gctgctcaga a                                              21

<210> SEQ ID NO 3
<211> LENGTH: 21
<212> TYPE: DNA
<213> ORGANISM: Artificial
<220> FEATURE:
<223> OTHER INFORMATION: Synthetic
```

```
<400> SEQUENCE: 3
cggattgagg agaaacgtaa a                                              21

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
agcccgtcta tgacaagaaa t                                              21
```